United States Patent [19]

Fischer

[11] Patent Number: 4,572,067
[45] Date of Patent: Feb. 25, 1986

[54] PETRI DISH IMPRINTING APPARATUS
[75] Inventor: Thomas Fischer, Zurich, Switzerland
[73] Assignee: Tecnomara AG, Zurich, Switzerland
[21] Appl. No.: 676,183
[22] Filed: Nov. 29, 1984
[30] Foreign Application Priority Data Nov. 29, 1983 [CH] Switzerland .................. 6376/83

[51] Int. Cl.⁴ ............................................. B41F 17/20
[52] U.S. Cl. .......................................... 101/7; 101/8; 101/29; 101/39
[58] Field of Search ................ 101/7, 8, 5, 40, 39, 101/35, 37, 9, 21, 25, 29, 31; 53/315, 316

[56] References Cited
U.S. PATENT DOCUMENTS

| | | | |
|---|---|---|---|
| 1,652,891 | 12/1927 | Davis | 101/21 |
| 2,077,970 | 4/1937 | Trunk | 101/37 |
| 2,205,399 | 6/1940 | Edwards | 101/21 |
| 2,316,517 | 4/1943 | Huntley et al. | 101/7 |
| 2,346,174 | 4/1944 | Malnar | 101/7 X |
| 2,386,797 | 10/1945 | Hohl et al. | 53/316 |
| 2,558,354 | 6/1951 | Gottscho | 101/8 |
| 2,891,468 | 6/1959 | Taylor et al. | 101/5 |
| 3,309,986 | 3/1967 | Worth | 101/39 |
| 3,486,442 | 12/1969 | Weber | 101/40 |
| 3,577,701 | 3/1971 | Bott et al. | 101/7 X |
| 3,718,085 | 2/1973 | Perret | 101/40 |
| 3,783,776 | 1/1974 | Noble et al. | 101/40 X |
| 3,922,964 | 12/1975 | Fisher | 101/9 |
| 4,098,183 | 7/1978 | Johnson | 101/40 |

Primary Examiner—Clifford D. Crowder
Attorney, Agent, or Firm—Karl F. Ross; Herbert Dubno

[57] ABSTRACT

A petri dish imprinting apparatus comprises an imprinting block of characters disposed along one side of a support surface for a covered petri dish and having heated characters adapted to imprint the petri dish by thermal embossment. An endless belt on the other side of the path presses the petri dish against the heated characters.

18 Claims, 4 Drawing Figures

PETRI DISH IMPRINTING APPARATUS

FIELD OF THE INVENTION

My present invention relates to an apparatus for imprinting petri dishes with identifying indicia, and more particularly, to an apparatus for marking petri dishes as they are displaced along a transport path.

BACKGROUND OF THE INVENTION

The identification of petri dishes and especially covered petri dishes which have received an aliquot of a nutrient, generally prior to innoculation with the microorganisms to be cultured therein and incubation, is important because identification of the culture medium and of characteristics of the project is vital to a proper evaluation of the results obtained and failure of proper identification may lead to a significant misinterpretation of results and time-comsuming procedures for analyzing them.

Such petri dishes generally have a flat bottom and an upwardly flaring circumferential wall rising from this bottom to a limited height. A cover, having a downwardly flaring circumferential wall or skirt, generally rests loosely on the upper rim of the wall of the bottom member with the skirt terminating above the bottom of the covered dish. Both members are composed generally of a transparent or glass-clear synthetic resin and can be injection molded or otherwise formed so as to be disposable.

Apparatus for the labeling of petri dishes onstream has been proposed heretofore, such apparatus applying indicia to the cover or upon the bottom of the petri dish, or as a label which is adhesively attached to the bottom or to the cover.

All such systems have various disadvantages.

Marking the bottom, for example, is frequently ineffective because the bottom of a petri dish in normal handling can become soiled, e.g. with the nutrient medium, so as to make the markings illegible.

Marking of the covers is unsatisfactory because the covers may be removed and various covers may become intermingled so that identification of the culture media in respective petri dishes can no longer be assured.

Adhesive labels may become loose and fall off during incubation or handling.

Consequently, the need for effective marking of petri dishes in an onstream automatic manner has not been satisfactorily resolved heretofore.

OBJECTS OF THE INVENTION

It is, therefore, the principal object of the present invention to provide an improved apparatus for the automatic onstream inscription of petri dishes, i.e. the automatic inscription of petri dishes on a transport path therefor, preferably downstream of a machine for filling the petri dishes with culture medium and covering them, whereby disadvantages of the prior art systems are avoided.

Another object of this invention is to provide an improved petri dish marking machine which can accurately, reproducibly and efficiently mark petri dishes in such manner that the risk of soiling of the markings, e.g. with nutrient medium, is minimized, that the danger of mix-up is eliminated, and that there is little if any impediment to the movement of petri dishes through the marking machine even when marking is not desired.

SUMMARY OF THE INVENTION

These objects are attained, in accordance with the invention, in an apparatus for inscribing covered petri dishes with identifying indicia which comprises means forming a support surface upon which a bottom of a petri dish can rest and along which this petri dish can be shifted, e.g. by movement of this surface which can form an upper stretch of a conveyor belt carrying petri dishes from a machine for supplying them with nutrient medium and applying a cover to each of them. Imprinting means in the form of a block is disposed at a generally fixed location to one side of this support surface and has heatable characters adapted to imprint a flaring circumferential wall of the petri dish upon rolling displacement of the wall of the petri dish along the block.

On an opposite side of the support surface, an endless conveying and pressing band yieldably bears against a cover of the petri dish and rolls the aforementioned wall of the dish against the block and induces this wall to roll along the block and to be imprinted with the characters which are thermally embossed in this wall of the thermoplastic petri dish below the skirt of the cover, but above the bottom of the dish. A holddown element engages the cover from above and therethrough presses the petri dish against the support surface at least in the region of the imprinting means.

With this apparatus, misplacing of the cover no longer results in a potential for mislabeling. Furthermore, since the imprint is a thermal embossing applied along the upright wall below the skirt of the cover, the indicia are more easily viewed and the danger of contamination is markedly reduced. Finally, with respect to the advantages of this apparatus, it will be apparent that the apparatus is comparatively simple and inexpensive, operating without color transfer so that the problems associated with loss of visibility of colored imprints do not characterize the invention.

According to a feature of the invention, the band is composed of a foamed synthetic resin. It has been found to be advantageous, moreover, to form the characters as individual stamping bars which can form part of a font of embossing faces and to provide these bars with recesses allowing them to rest upon and partly embrace a heating rod or bar which transfers heat by conduction to the stampers. Furthermore, it has been found to be advantageous to orient the block or array of stampers so that they are inclined downwardly toward the support surface inwardly. This ensures a downward component of pressure during embossment as the lower shell of the petri dish rolls along the block to assist in retaining the petri dish against the support surface.

An especially simple method of changing the characters is thereby provided since the individual stampers need only be replaced by others from a set to change the legend which is to be embossed on the petri dish.

Alternatively, the characters can be provided on respective endless strips lying in planes perpendicular to the imprint plane formed by the array of characters against which the petri dish wall is caused to roll, each of these endless strips being provided in turn with a respective selector adapted to position the selected character in this imprinting plane.

While this system is somewhat more complex, it eliminates the need to provide a store of stampers. It also has the advantage that the selection of the characters can be remotely controlled and has been found to be especially useful for the application of a sequence of serial numbers.

According to another feature of the invention means is provided for adjusting the force with which the holddown element, e.g. a roller, bears upon the cover of the petri dish, and means is also provided, in addition or alternatively, for adjusting the height of the holddown roller above the support surface. This likewise minimizes the danger of an improper imprint.

I can also provide an abutment along the one side of the support surface at which the block is provided and against which the wall of the petri dish can roll under the action of the yieldable band when no imprint is desired but a continuous displacement of the petri dishes as part of a filling and handling process for the petri dishes is provided and the imprinting unit is positioned along a line for handling the petri dishes. Beyond the imprinter, any other desired steps can be carried out, e.g. the petri dishes can be stacked and stored awaiting innoculation.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 2:
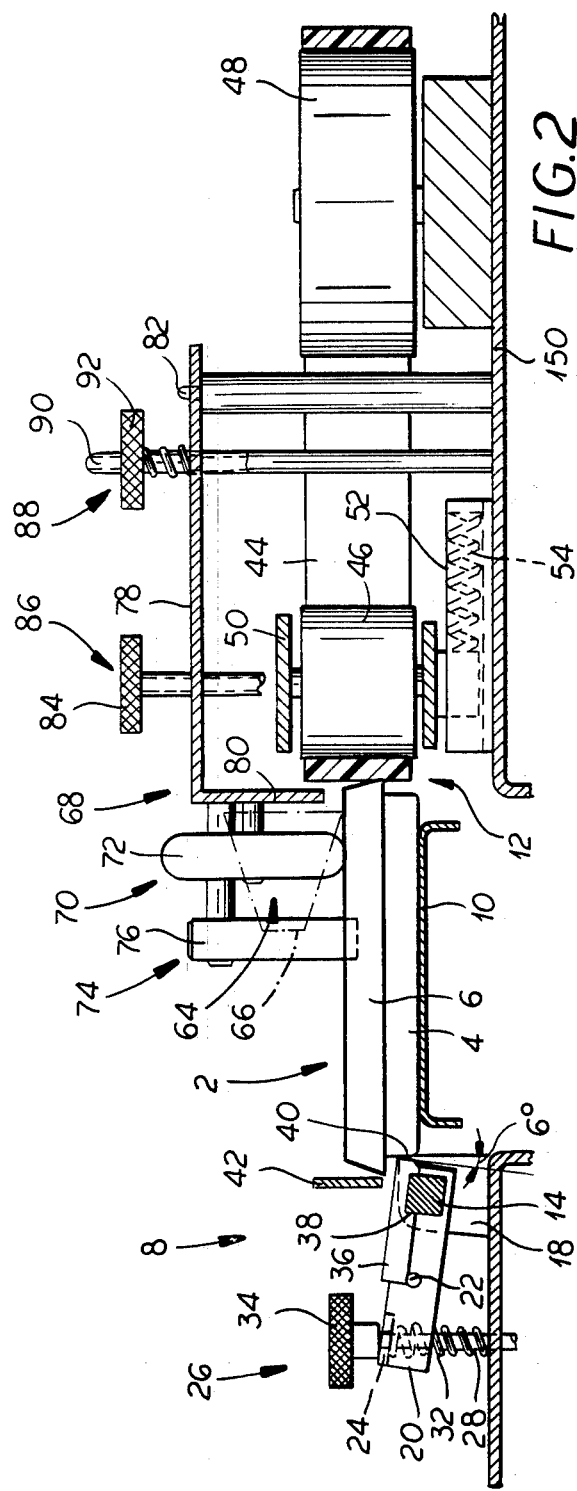
FIG. 2 is a section taken along the line II—II of FIG. 1.
Figure 4:
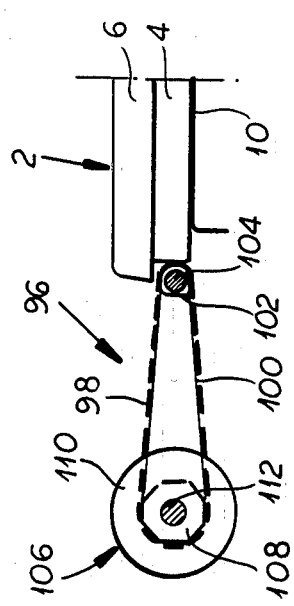
FIG. 4 is a section taken along the line IV—IV of FIG. 3.

The apparatus shown in the drawing is intended to imprint, by thermal embossing, the upwardly flaring circumferential wall of a lower shell 4 of a petri dish 2 whose cover 6 has a downwardly flaring circumferential wall or skirt partly overhanging the circumferential wall which is to be imprinted (see FIGS. 2 and 4). The petri dishes are generally composed of glass-clear thermoplastic synthetic resins.

Figure 1:
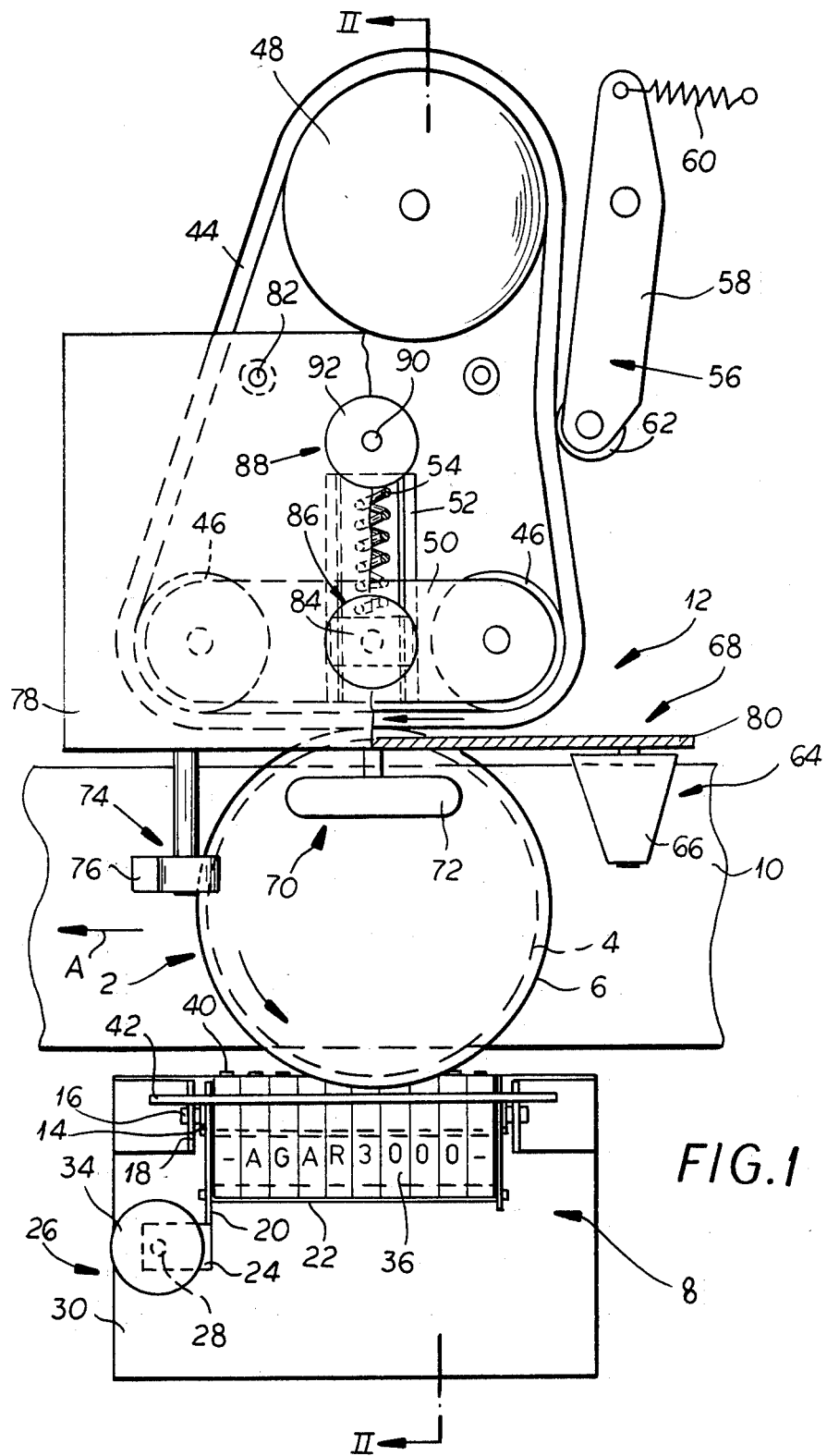
FIG. 1 is a plan view, partly broken away, of an imprinting station along a petri dish filling line and embodying the invention.

The apparatus shown in FIGS. 1 and 2 comprises an imprinting unit 8 in the form of a stationary block along which the petri dishes can move on a support surface 10, e.g. an endless conveyor which can run from a filling and covering machine at the right hand side (FIG. 1) to a stacking machine at the downstream side, i.e. to the left in FIG. 1. Along the opposite side of the support surface 10 a conveyor and pressing unit 12 is provided which serves not only to cause the petri dish 2 to roll against the imprinting block 8, but also provides the pressure with which the wall of the petri dish is embossed.

The imprinting unit 8 comprises a heated bar or rod 14 which can be a resistance-heating unit connected to a source of electric current. This bar is pivotal about journal pins 16 in support arms 18. The heating bar 14 is also provided with a pair of arms 20 spanned by a pin 22 and one of which is elongated to have a flange 24 associated with a tilt-adjusting unit 26. The tilt-adjusting unit 26 includes a threaded spindle 28 which is received in a base plate 30 and, upon rotation of its knurled knob 34 can swing the arms 20 about the pivot 16 to adjust the tilt of a plurality of stamping bars 36 which rest upon the bar 14 and the rod 22.

More particularly, a spring 32 is pressed against the base plate 30 into which the spindle 28 is threaded and bears upwardly against the flange 24, holding it against the knob 34.

The imprinting bars 36 are formed at their ends with the characters 40 to be imprinted or embossed upon the petri dish in complementary form. For the sake of identification, these characters are also represented at the tops of the bars as can be seen in FIG. 1 and, reading from left to right, can include a dash, the letter A, the letter G, and so on as shown to define, for example, the medium in the petri dish.

Each bar 36, which is composed of metal and thus is heated by conduction from the heating bar 14, is formed with a recess 38 partly receiving the bar 14 so as to be in effective heat conductive relationship therewith.

As illustrated in FIG. 2, the stampers 36 are adjusted to an inclination with respect to the support surface 10, e.g. include an angle of about 6° with the horizontal, so that when the characters 40 emboss the wall of the petri dish below the cover apron, the downward component of force is applied to hold the petri dish against the surface 10.

Above the stampers 36, I provide an abutment 42 in the form of a bar which can support the skirt of the cover 6 of the petri dish when the imprinting block 8 is retracted or removed because no imprint is desired but is is nevertheless advantageous to keep the printing unit in place and permit the movement of the petri dishes therepast in a continuous manner.

The conveyor and pressing unit 12 comprises an endless band 44 which bears against the skirt of the cover 6 on the side of the support surface 10 opposite that at which the imprinting unit 8 is provided. The band 44 passes over a pair of spaced apart deflection rollers 46 and around a drive roller 48 which may be continuously driven by an electric motor (not shown). The roller pair 46 may be bridged by a yoke 50 which is guided for movement perpendicular to the path of the petri dishes from right to left along the apparatus shown in FIG. 1 by a prismatic guide 52. The guide 52 allows the yoke to be biased in a direction perpendicular to the path along the support surface 10 by a compression spring 54 providing the pressing force for the section of the band 44 between the rollers 46 against the apron of the cover 6.

Slack in the belt is taken up by a compensating unit 56 which maintains the belt tension. The unit 56 comprises a lever 58, one arm of which is engaged by a tension spring 60 while the other arm carries a roller 62 bearing against the belt. The belt is composed preferably of a foamed rubber or foamed synthetic resin to conform readily to the peripheral configuration of the petri dish. The belt thus presses the petri dish to the left, as seen in FIG 2, via its cover 6 and against the imprinting unit 8 while causing the petri dish to roll along the imprinting unit 8 as it is advanced in the direction of arrow A.

In the event the cover has not been seated properly upon the shell 4 of the petri dish, a frustoconical roller 66 forming part of a cover orienting unit 64 is provided at the upstream side of the imprinting station. The roller 66 is mounted upon a holder 68 which can be raised and lowered to ensure that the roller 66 can engage a cover positioned improperly so that as the cover moves past this roller, it rides along the frustoconical surface and drops into place.

The same holder or bracket 68 carries the holddown element 70 which includes a roller 72 resting against the cover 6 and serving to brace the entire petri dish at least lightly against the surface 10.

On the downstream side, a further holddown element 74 in the form of a pivotal lever 76 is engageable with the cover of the petri dish and is positioned so that as the trailing edge of the cover passes under the roller 72, member 76 will rest upon the cover and prevent it from being lifted. The bracket 68 comprises an angled plate 78 which is formed with a downwardly extending flange 80 at its side turned toward the support surface 10 and upon which the roller 72 and the lever 76 are mounted. The roller 66 is likewise journaled on this flange.

The plate 78 is swingably mounted on a pin 82 remote from the flange 80. An adjusting screw 84, broken away in FIG. 2, can extend through a slot in the yoke to bear against the plate 150 supporting the assembly and hence adjust the height of the roller 72 and elements 66 and 76. The force with which these elements are downwardly biased is controlled by an adjusting unit 88 including a knurled nut 92 threaded onto a stationary rod 90 passing with clearance through the plate 78 and stressing a spring 94 against this plate.

The alteration of the character set applied to the petri dish is effected in the embodiment of FIGS. 1 and 2 simply by replacing the stampers 36. A thermostat, not shown, can be used to control the temperature and hence the heating of these stampers.

Figure 3:
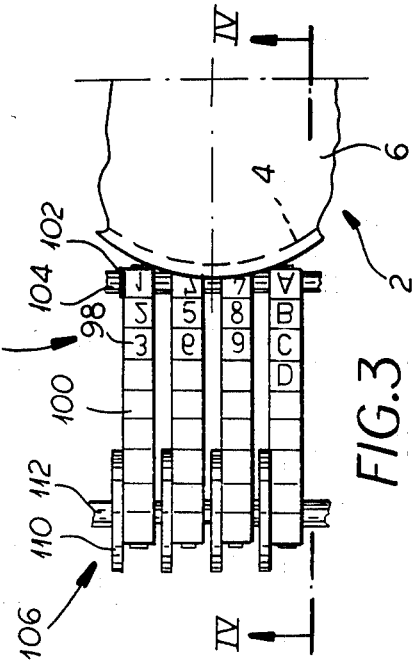
FIG. 3 is a plan view of the embossing block in accordance with another embodiment of the invention.

In FIGS. 3 and 4 where the apparatus is the same except for the imprinting unit, the imprinting device 96 comprises endless strips 100 carrying the individual characters 98 and lying in respective planes transverse to the imprinting plane, i.e. the plane of the line of characters along which the petri dish rolls.

As in the embodiment of FIGS. 1 and 2, the endless strips 100 are carried by pivotal members 102 which are rotatable on the heating bar 104. Individual setting units 106 are provided for each of the strips 100 to select the character positioned in the imprinting plane.

Each of these units 106 can comprise a prismatic roller 108 over which the strip passes and which is rotatably connected to a respective setting wheel 110, the setting wheels and prismatic rollers being mounted on a common shaft 112. Naturally, instead of manually settable wheels, I can make use of motor-driven or electronically set wheels and provide a remotely controlled or automatic character resetting device.

I claim:

1. An apparatus for inscribing identifying indicia onto a circumferential wall of a petri dish covered by a cover loosely seated on said wall and having a circumferential skirt partly overhanging said wall, comprising:
    means forming a support surface upon which a bottom of a covered petri dish can rest and along which said petri dish can be shifted;
    imprinting means in the form of a block disposed at a generally fixed location along one side of said support surface and having heatable characters adapted to imprint said wall of said petri dish upon rolling displacement of said wall of said petri dish along said block;
    an endless conveying and pressing band yieldably bearing laterally against said skirt of said cover of said petri dish on the opposite side of said support surface for urging said wall against said block and inducing said wall to roll against said block whereby said wall is thermally embossed with imprints of said characters; and
    a holddown element for pressing said cover down onto said petri dish and thereby to press said petri dish against said support surface at least in the region of said imprinting means, said holddown element comprising a roller rotatable about an axis transverse to the direction of movement of said petri dish and bearing on said cover from above and a device for adjusting the force with which said roller bears against said cover.

2. The apparatus defined in claim 1 wherein said band is composed of a foamed synthetic resin material.

3. The apparatus defined in claim 1 wherein said characters are inclined to said support surface, in a direction tending to apply a force component holding said petri dish against said support surface as said wall is imprinted with said characters.

4. The apparatus defined in claim 3, further comprising means for adjusting the angle of inclination at which said characters are oriented to said support surface.

5. The apparatus defined in claim 1 wherein said characters are replaceable embossing stamps mounted on said block.

6. The apparatus as defined in claim 5 wherein each stamp has a recess receiving a heating bar upon which said stamp is disposed.

7. The apparatus as defined in claim 6 wherein said stamps are inclined to said support surface.

8. The apparatus as defined in claim 1 wherein said characters are provided upon respective endless strips lying in planes transverse to an imprinting plane of said block, each of said strips being provided with means for displacing the respective strip to position selected characters thereof in said imprinting plane.

9. The apparatus as defined in claim 1, wherein said device comprises means for adjusting the height of said holddown element above said support surface.

10. The apparatus as defined in claim 1, further comprising an abutment positionable to engage said cover of said petri dish along said one side of said support surface when no imprint is desired and adapted to allow said band to roll said petri dish along said abutment.

11. The apparatus as defined in claim 10 wherein said band is provided with a pair of idler rollers disposed on said other side of said support surface along the path of movement of said petri dish and with a drive roller spaced from said pair of idler rollers, said band passing around said drive roller and said idler rollers.

12. The apparatus as defined in claim 11, further comprising spring means for urging said pair of idler rollers toward said block.

13. An apparatus for inscribing identifying indicia onto a circumferential wall of a petri dish covered by a cover loosely seated on said wall and having a circumferential skirt partly overhanging said wall, comprising:
    means forming a support surface upon which a bottom of a covered petri dish can rest and along which said petri dish can be shifted;
    imprinting means in the form of a block disposed at a generally fixed location along one side of said support surface and having heatable characters adapted to imprint said wall of said petri dish upon rolling displacement of said wall of said petri dish along said block;
    an endless conveying and pressing band yieldably bearing laterally against said skirt of said cover of said petri dish on the opposite side of said support surface for urging said wall against said block and inducing said wall to roll against said block whereby said wall is thermally embossed with imprints of said characters, said band being provided with a pair of idler rollers disposed on said other side of said support surface along the path of movement of said petri dish and with a drive roller spaced from said pair of idler rollers, said band passing around said drive roller and said idler rollers, and said band further having associated therewith spring means for urging said pair of idler rollers toward said block;

an abutment positionable to engage said petri dish along said one side of said support surface when no imprint is desired and adapted to allow said band to roll said petri dish along said abutment; and a holddown element for pressing said petri dish against said support surface at least in the region of said imprinting means, said holddown element comprising a pressing roller bearing upon said cover of said petri dish and mounted on a plate overlying said pair of idler rollers, means for adjusting the height of said plate relative to said support surface, and means for adjustably biasing said plate yieldably downwardly to control the force exerted by said pressing roller of said holddown element against said cover.

14. The apparatus as defined in claim 13 wherein said band is composed of a foamed synthetic resin.

15. The apparatus as defined in claim 14, further comprising a spring biased tensioning roller bearing upon said band for maintaining it taut.

16. The apparatus as defined in claim 15, further comprising a frustoconical roller upstream of said holddown element along the path of said petri dish on said support surface for engagement with said cover to ensure that said cover is properly seated on the petri dish before it reaches said pressing roller.

17. The apparatus as defined in claim 16, further comprising a swingable lever downstream of said holddown element for preventing the lifting of said cover as said petri dish passes from beneath said pressing roller along said path.

18. The apparatus as defined in claim 17 wherein said path is provided downstream of a petri dish filling machine.

* * * * *